(12) United States Patent
Bachus et al.

(10) Patent No.: US 6,385,480 B1
(45) Date of Patent: May 7, 2002

(54) ANGIO-MR SYSTEM

(75) Inventors: Reiner Bachus, Neunkirchen; Knut Imhof; Rainer Kuth, both of Herzogenaurach; Michael Pflaum, Adelsdorf, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/483,692

(22) Filed: Jan. 14, 2000

(30) Foreign Application Priority Data

Jan. 15, 1999 (DE) .......................... 199 01 482

(51) Int. Cl.[7] ................................ A61B 5/05
(52) U.S. Cl. .................. 600/411; 600/427; 378/62; 378/63
(58) Field of Search ................. 600/411, 415, 600/427, 407; 250/390.02; 378/63, 62; 324/318, 322

(56) References Cited

U.S. PATENT DOCUMENTS

| | | | | |
|---|---|---|---|---|
| 4,328,418 A | * | 5/1982 | Morgan et al. | |
| 4,758,812 A | * | 7/1988 | Forster et al. | |
| 5,525,905 A | * | 6/1996 | Mohapatra et al. | |
| 5,530,425 A | | 6/1996 | Harrison | |
| 5,615,430 A | | 4/1997 | Nambu et al. | |
| 5,735,278 A | * | 4/1998 | Kawasaki et al. | |
| 6,101,239 A | * | 8/2000 | Kawasaki et al. | |
| 6,131,690 A | * | 10/2000 | Galando et al. | |

* cited by examiner

Primary Examiner—Marvin M. Lateef
Assistant Examiner—Talaya G James
(74) Attorney, Agent, or Firm—Schiff Hardin & Waite

(57) ABSTRACT

A multiple examination arrangement has a number of imaging systems that are arranged at one location such that a patient lying on a movable patient support table can be examined in each of the imaging systems without changing beds. One of the imaging systems is a magnetic resonance system having an actively shielded magnet, another is a radiographic angio system, preferably offset laterally relative to the z-axis of the magnet. Selected components of the angio system have a soft-magnetic covering as shielding against the static stray field of the MR system.

9 Claims, 2 Drawing Sheets

ANGIO-MR SYSTEM

BACKGROUND OF THE INVENTION

1. Field of the Invention

The present invention relates to a multiple examination arrangement of the type having a number of imaging systems that are located in one space such that a patient lying on a movable patient support table can be examined in each of the imaging systems without changing beds.

2. Description of the Prior Art

Multiple examination arrangements such as the type described above have been proposed many times. Besides the combination described in U.S. Pat. No. 5,615,430 of a linear accelerator with a computed tomography system, other combinations of imaging systems have already been contemplated. A common drawback of all these proposals is that they have not been designed to give adequate consideration to the mutual influence of the systems, and in none of these proposals are any specific measures taken to avoid interference effects of the fields of one system on the other systems.

SUMMARY OF THE INVENTION

An object of the present invention is to provide a multiple examination arrangement that is suitable for medical diagnosis, particularly for interventional diagnosis, which offers the additional advantage of a more extensive use for simultaneously examining different patients, besides the simplified examining of one patient in several imaging systems.

This object is inventively achieved in a multiple examination arrangement that, besides an MR system having an actively shielded magnet, has a radiographic angiography system having a soft-magnetic covering for shielding from the static stray field of the MR system. The radiographic angiography system preferably is laterally offset relative to the z-axis of said magnet of the MR system.

The combination of an MR system with a radiographic angiography system represents the unification of two particularly essential imaging systems for medical diagnosis whose simultaneous utilization in one examination space has not been accomplished heretofore due to the strong fields that influence the other device.

The construction of the MR device with an actively shielded magnet—so that only a quadrupolar stray field that decays rather sharply with distance can penetrate beyond the shielding—together with the displacement of the radiographic angiography system laterally relative to the z-axis of the magnet of the MR system, combined with the additional soft-magnetic shielding of the imaging parts of the radiographic angiography system, achieve a mutual decoupling of such a nature as to enable simultaneous operation of both systems in one space without significant mutually interfering influences.

In an embodiment of the invention the magnet of the MR system is provided with a field stabilizing system (E.I.S.) that has ferromagnetic coils at the face sides of the magnet. This compensates for interfering influences on the field homogeneity in the center of the magnet caused by ferromagnetic parts, particularly moving or shifted parts, in the environment i.e., it prevents undesirable feedback caused by the shielding parts of the radiography system.

The ferromagnetic shielding elements at the radiographic angiography system should be arranged substantially symmetrically around the axis, or corresponding balancing elements should be installed, so that, as a consequence of the symmetry in rotational movements, the magnetic resonance magnets optimally do not exert any influence on the homogeneity from the outset.

In addition to these shieldings as described above, it has proven particularly expedient to shield the electronics of the radiographic angio system at least partially against emerging electromagnetic interference radiation, and to construct the electronics such that its unshielded regions can be separately shut off and/or deactivated into a "sleep mode." In this way, no electromagnetic interference radiation can influence the measuring of the magnetic resonance signals.

At least in the regions of the support table in which the patient lying thereon is to be X-rayed, the patient support table should consist of a material that is MR-compatible, particularly a material having a low electrical conductivity and a small loss factor, and which is non-ferromagnetic. Furthermore, the material should exhibit only a low X-ray absorption, and should be substantially homogenous.

Based on this construction of the patient support table, it is also possible for the patient support table to be provided in a particularly simple manner with longitudinally displaceable removable plates and to be mounted on a column that can be rotated around the intersection of the insertion axes of the magnetic resonance system and the radiographic angiography system. It has proven particularly advantageous to construct the top support table plate of the patient support table as the insertion transport plate for the magnetic resonance system.

Based on this particular type of allocation of the MR system and the radiographic angio system relative to one another and of the patient support table that can be moved into position for insertion into both imaging systems by simple rotation around the column, a particularly simple and rapid examination sequence is possible, which is of importance in view of the high cost of such systems and the high degree of utilization thereof thus required.

DESCRIPTION OF THE PREFERRED EMBODIMENTS

Figure 1:
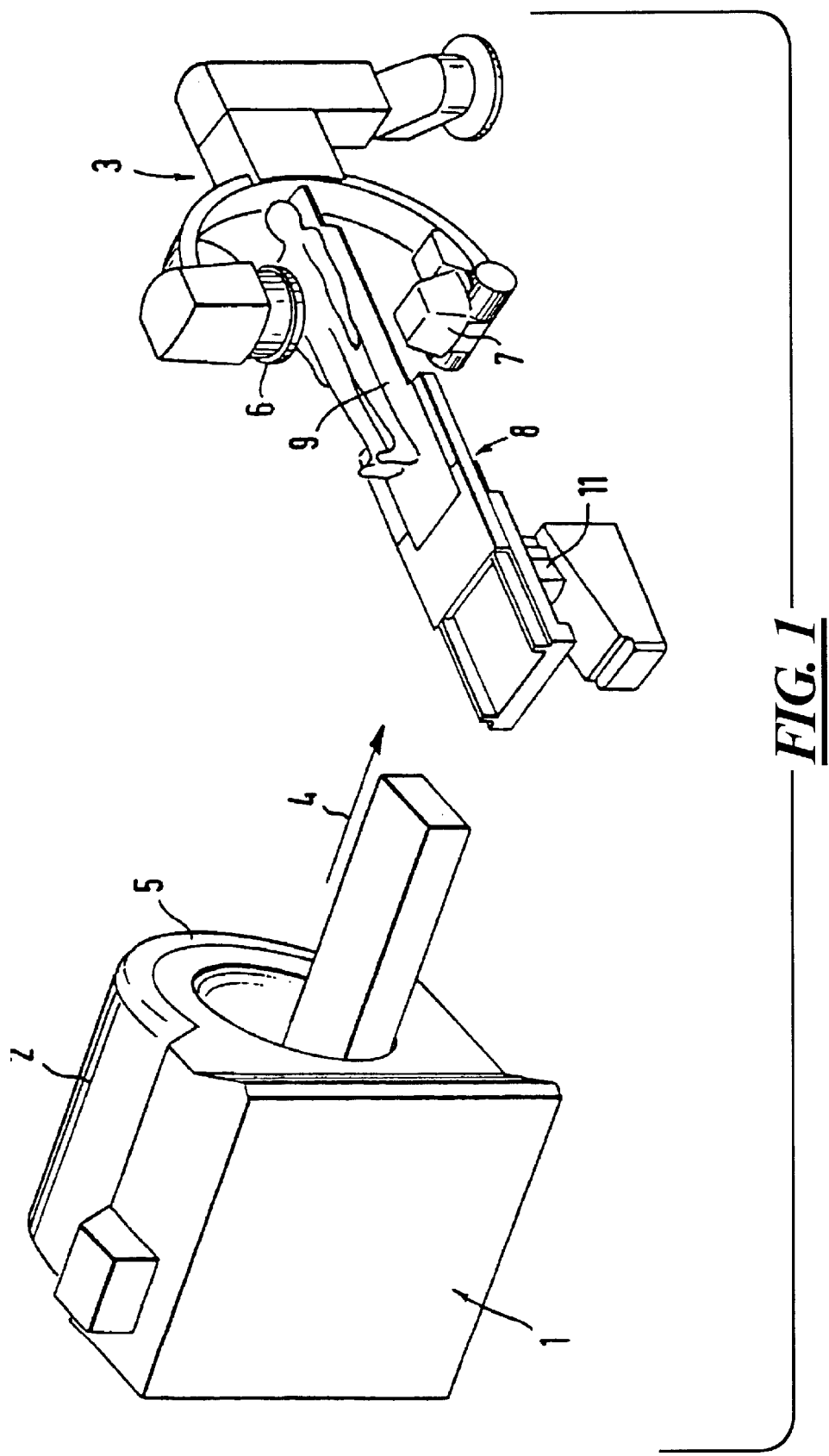
FIG. 1 shows an inventive multiple examination arrangement having a magnetic resonance system and a radiographic angio system, and a patient support table that can be rotated around a column, in a first examination position of the patient examination table.
Figure 2:
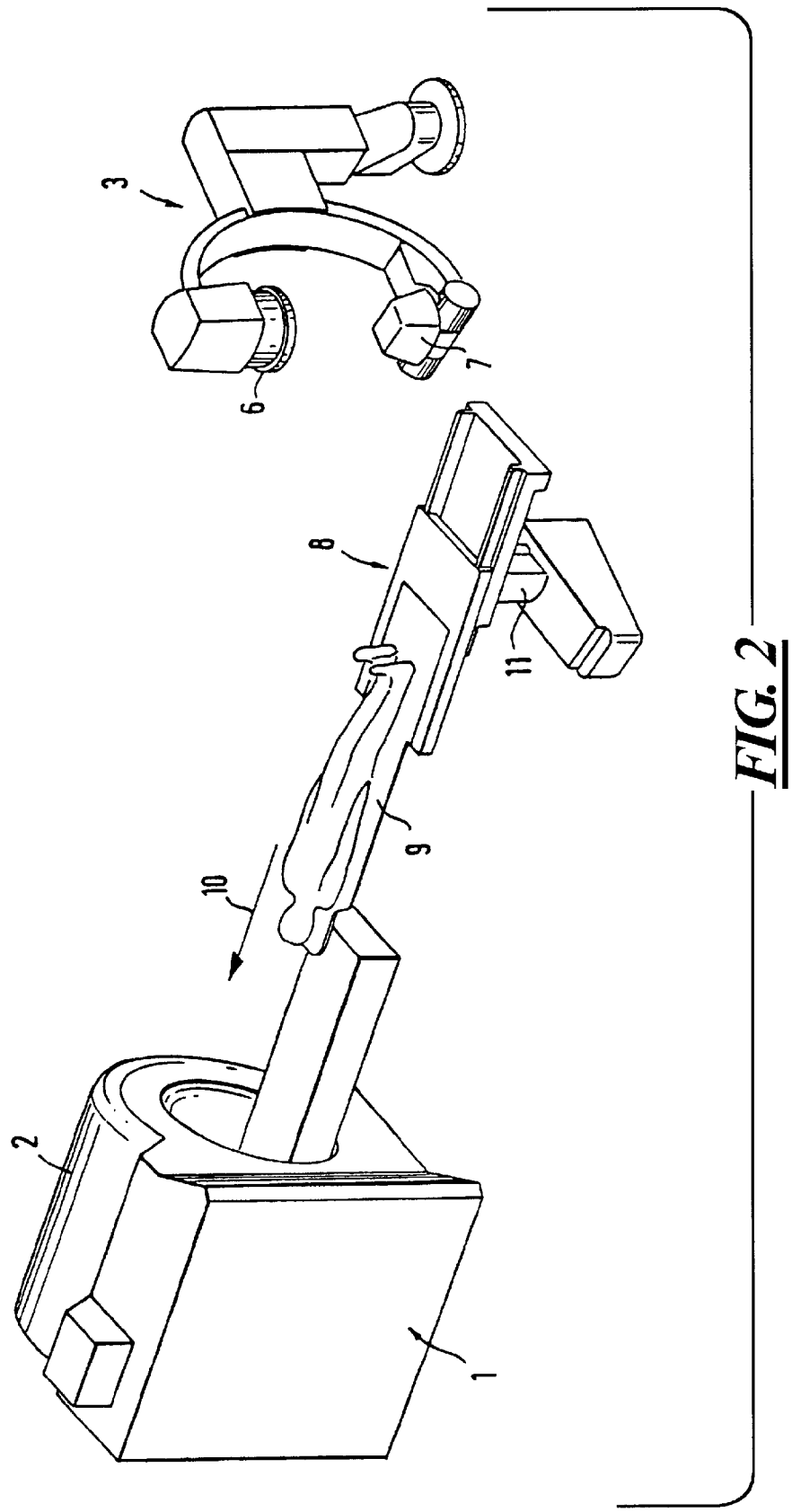
FIG. 2 shows the inventive multiple examination arrangement in the second examination position of the patient support table.

The depicted magnetic resonance system is provided with a magnet 2 that is actively shielded by surrounding the coil which generates the magnetic field in the center of the MR system 1 with a second coil in which current flows in the opposing direction. This shields the inner field so that the far field of the magnet is still a quadrupolar field that decays with the fourth power of the distance. As a result, interfering influences of the magnetic field of the MR system on the radiographic angio system 3 are appreciably reduced from the outset, not only because this is arranged some distance from the MR system 1, but also because its important imaging system is disposed at an appreciable lateral offset in relation to the z-axis 4 of the MR system 1. The z-axis 4 coincides with the axis of insertion. The magnet 2 of the MR system 1 is additionally provided with a field stabilizing system (EIS) formed by ferromagnetic coils at the face sides 5, which shields magnetic field in the center of the magnet 2 from interference effects which disrupt the field homogeneity, caused by ferromagnetic parts in the environment. Such ferromagnetic parts include ferromagnetic parts which are arranged in the region of the important imaging components 6 and 7 of the radiographic angio system 3 in order to completely shield them from the small, though not entirely negligible stray fields of the magnet 2 of the MR system 1. Feedback from these moving ferromagnetic parts to the MR system 1 is prevented by the above described EIS. The soft-magnetic shieldings of the regions of the components 6 and 7 of the radiographic angio system 3 are arranged symmetrically around the axis, or corresponding balancing elements are installed, so that as a consequence of the symmetry, in rotational motions of the angio system 3 the homogeneity of the magnetic resonance magnet 2 is not influenced.

The patient support table 8 is provided with longitudinally displaceable, removable plates, the top plate 9 of which is constructed as insertion transport plate for the MR system 1, which is indicated in FIG. 3 by the arrow 10, along which the patient is inserted into the MR system I on this top support table plate 9.

The patient support table is mounted on a rotating column 11, whose vertical axis of rotation is situated in the intersection of the respective axes of insertion of the MR system 1 and the radiographic angio system 3. Thus, a mere pivoting of the patient support table around the axis of the column 11 is required in order to change from one examination system to the other, without any additional transport movement, which simplifies the system change over appreciably and shortens the examination item accordingly.

The overall electronics of the radiographic angio system 3 are shielded so that electromagnetic interference radiation cannot influence the measuring (pick-up) of the magnetic resonance signals. Alternatively or additionally the electronics can be constructed such that at least portions thereof can be switched off separately in unshielded areas, or can be switched into a sleep mode during the MR measurements.

Although modifications and changes may be suggested by those skilled in the art, it is the intention of the inventors to embody within the patent warranted hereon all changes and modifications as reasonably and properly come within the scope of their contribution to the art.

We claim as our invention:

1. A multiple examination arrangement comprising:

a plurality of imaging systems disposed at a common location, including a magnetic resonance imaging system and a radiographic angio system;

a movable patient support table disposed relative to said imaging systems so that a patient on said movable patient support table can be successively examined in each o said imaging systems without leaving said movable patient support table;

said magnetic resonance system having an actively shielded magnet having a z-axis and having a static stray field associated therewith; and said radiographic angio system being disposed at said common location laterally offset relative to said z-axis of said magnet, and containing selected components at least partially surrounded by a soft-magnetic covering for shielding said selected components from said static stray field.

2. A multiple examination arrangement as claimed in claim 1 wherein said magnetic resonance system further comprises a field stabilizing system for said magnet, said field stabilizing system comprising ferromagnetic coils respectively disposed at face sides of said magnet.

3. A multiple examination arrangement as claimed in claim 1 wherein said radiographic angio system has at least one axis and further comprising ferromagnetic shielding elements symmetrically distributed relative to said axis of said radiographic angio system.

4. A multiple examination arrangement as claimed in claim 1 wherein said radiographic angio system comprises electronics, and further comprising an electromagnetic interference radiation shield at least partially surrounding said electronics.

5. A multiple examination arrangement as claimed in claim 4 wherein said electronics include a circuit portion disposed in an unshielded region of said electronics, and a remainder of said electronics, and wherein said portion of said electronics in said unshielded region is switchable to an off state separately from said remainder of said electronics.

6. A multiple examination arrangement as claimed in claim 4 wherein said electronics include a circuit portion disposed in an unshielded region of said electronics, and a remainder of said electronics, and wherein said portion of said electronics in said unshielded region is switchable to a sleep mode separately from said remainder of said electronics.

7. A multiple examination arrangement as claimed in claim 1 wherein said patient support table, at least in a portion thereof in which said patient is to be subjected to X-rays in said radiographic angio system, consists of a magnetic resonance-compatible material having a low electrical conductivity and a small loss factor, and which is non-ferromagnetic.

8. A multiple examination arrangement as claimed in claim 1 wherein said magnetic resonance system has a patient insertion axis substantially coinciding with sa id z-axis, and wherein said radiographic angio system has a patient insertion axis which intersects said patient insertion axis of said magnetic resonance system, and wherein said patient support table comprises a column rotatable around the intersection of the respective insertion axes of said magnetic resonance system and said radiographic angio system, and further comprises a plurality of removable plates mounted on said column.

9. A multiple examination arrangement as claimed in claim 8 wherein said patient support table comprises a top one of said removable plates comprising an insertion transport plate for said magnetic resonance system.

* * * * *